United States Patent [19]
Edens et al.

[11] Patent Number: 5,808,737
[45] Date of Patent: Sep. 15, 1998

[54] PRE-ANALYSIS CHAMBER FOR A FLOW PARTICLE ANALYZER

[75] Inventors: Carl T. Edens, Severna Park; Joseph Katz, Baltimore, both of Md.

[73] Assignee: Sienna Biotech, Inc., Columbia, Md.

[21] Appl. No.: 805,764

[22] Filed: Feb. 25, 1997

Related U.S. Application Data

[60] Provisional application No. 60/012,496 Feb. 29, 1996.
[51] Int. Cl.$^6$ .............................. G01N 1/10; G01N 15/02; G01N 21/00
[52] U.S. Cl. ........................... 356/246; 356/336; 356/338
[58] Field of Search ..................... 356/246, 39, 72–73, 356/336, 338

[56] References Cited

U.S. PATENT DOCUMENTS

| | | |
|---|---|---|
| 3,662,176 | 5/1972 | Kamentsky et al. . |
| 4,660,971 | 4/1987 | Sage et al. . |
| 4,781,459 | 11/1988 | Suzuki . |
| 4,790,653 | 12/1988 | North, Jr. . |
| 4,997,275 | 3/1991 | Gaucher et al. . |
| 5,007,732 | 4/1991 | Ohki et al. . |
| 5,030,002 | 7/1991 | North, Jr. . |
| 5,579,107 | 11/1996 | Wright et al. ........................... 356/336 |

*Primary Examiner*—Frank G. Font
*Assistant Examiner*—Amanda Merlino
*Attorney, Agent, or Firm*—Lerner, David, Littenberg, Krumholz & Mentlik

[57] ABSTRACT

A pre-analysis chamber having reduced turbulence is provided for a flow particle analyzer. The chamber has a conical diverging section for decelerating sheath fluid flow to form a laminar profile, followed by a conical converging section for accelerating flow. A sample inlet tube is supported in the chamber near the interface between the diverging and converging sections, and terminates in the laminar, accelerated sheath flow. The sample enters the laminar sheath flow to form a discrete sample stream.

30 Claims, 4 Drawing Sheets

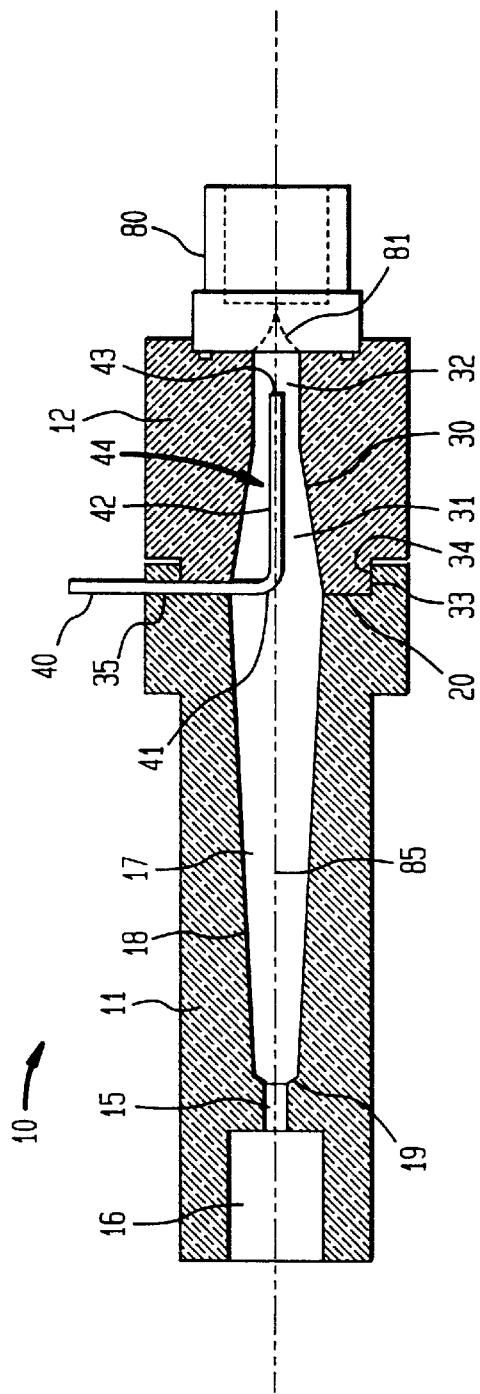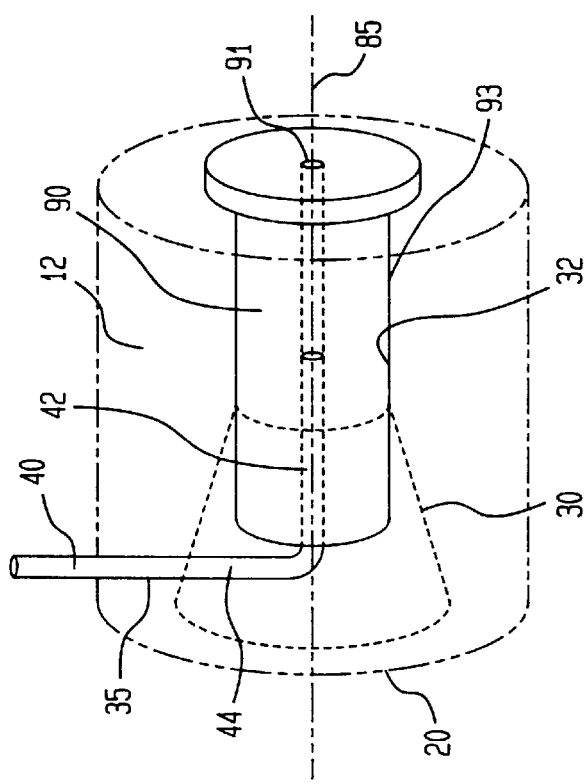

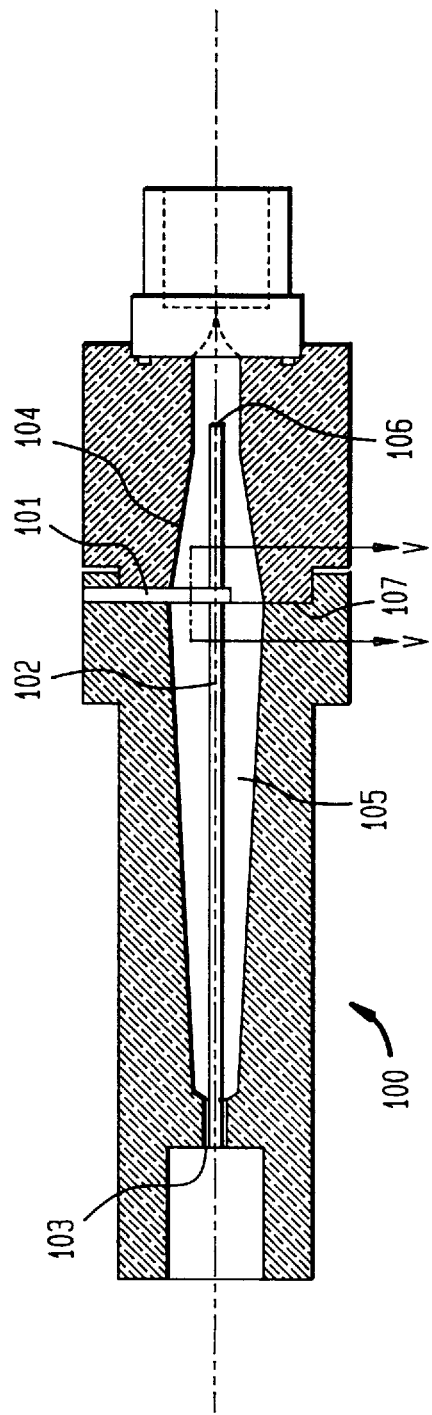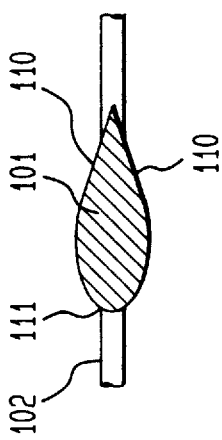
FIG. 4
FIG. 5

PRE-ANALYSIS CHAMBER FOR A FLOW PARTICLE ANALYZER

The present application claims the benefit of United States Provisional Application No. 60/012,496 filed on Feb. 29, 1996.

BACKGROUND OF THE INVENTION

The present invention relates generally to flow particle analysis, also known as flow cytometry, a technique for optically measuring characteristics of particles.

In this technique, particles are presented for analysis by encasing a thin stream of a particle suspension in a stream of a sheath fluid and passing the combined streams through an optical analysis chamber. In the optical analysis chamber, a light beam such as a laser beam intersects the combined streams. Light absorbed or scattered by the particles can be measured to count particles or to measure characteristics of the particles. One application of this technique is in counting blood cells and categorizing them by their light-scattering properties. This technique is also employed in biochemical assays. Particles such as latex microspheres or colloidal gold particles are coated with materials which interact with a substance to be assayed in blood or other bodily fluids. Depending upon the particular substance, the interaction may cause the particles to agglutinate with one another, or may retard agglutination. In either case, the number of agglutinated particles present after the particles are reacted with the bodily fluid will indicate the amount of the substance present.

It is important to position the stream of sample fluid precisely in the analysis chamber, so that the particles pass through the beam of light at a stable position near the center of the beam. To provide such precise positioning, the sample fluid stream must be accurately positioned within the stream of sheath flow liquid. Also, the sample fluid, and the sheath fluid surrounding it, should flow into the analysis chamber in a smooth, laminar manner, without appreciable turbulence. The present invention relates to apparatus and methods for introducing the sample suspension into the sheath flow.

The device used to introduce the sample suspension into the sheath flow is commonly referred to as a "pre-analysis chamber." Pre-analysis chambers in which a sample inlet tube passes through a sheath fluid reservoir are known. For example, Gaucher, et al., U.S. Pat. No. 4,997,275, discloses a flow cell having a chamber upstream of the optical analysis section, into which the sheath and the sample are introduced. The chamber is of two-piece construction having frustoconical ends. The sheath fluid and the sample are introduced in two parallel tubes. The sample tube protrudes into the chamber and is unsupported, limiting the size of the chamber and also limiting the accuracy within which the sample tube can be positioned in the sheath fluid flow.

Ohki, et al., U.S. Pat. No. 5,007,732, discloses a flow chamber with a substantially rectangular cross section. The inlet is supported along its full length. The sheath fluid is introduced in a direction perpendicular to flow through the flow cell, requiring a bend in the sheath flow path.

North, Jr., U.S. Pat. No. 5,030,002, discloses a pre-analysis chamber with a long, unsupported sample inlet tube. Sheath fluid is introduced through a fluid connector positioned perpendicular to the flow.

North, Jr., U.S. Pat. No. 4,790,653, discloses a pre-analysis chamber having a diverging taper for introducing sheath flow perpendicular to the flow through the optical analysis area. A long, unsupported tube for introducing the sample extends from one end of the chamber.

Sage, et al., U.S. Pat. No. 4,660,971, discloses a pre-analysis chamber having a rectangular cross section and a converging taper. The sheath fluid is introduced perpendicular to the primary flow through the flow cell. The sample is introduced through a tube passing through a sidewall of the chamber and having a bend. The sample tube is provided with a support that can be adjusted to center the sample flow in the sheath liquid.

SUMMARY OF THE INVENTION

One aspect of the invention provides a pre-analysis chamber defined by a chamber wall having diverging and converging portions with their respective large ends interconnected, a sheath fluid inlet connected to the small end of the diverging portion, a sample inlet tube extending centrally within the converging portion of the chamber wall, and a transverse support for the sample inlet tube extending from the chamber wall adjacent the large ends of the converging and diverging portions. Because the region of the chamber adjacent the large ends of the converging and diverging wall portions has a large cross sectional area, the sheath fluid flows relatively slowly in this region. Therefore, the support extending from the chamber wall in this region creates only a small disturbance in the flow. Stated another way, it is possible to provide support for the sample fluid inlet tube in a region having low velocity and correspondingly low Reynolds number, resulting in an induced wake having reduced size, instability and momentum deficit. Preferred pre-analysis chambers according to this aspect of the invention can be simple and economical to manufacture, and yet can provide accurate positioning of the sample suspension stream within the sheath fluid stream.

The transverse support for the sample inlet tube may comprise a portion of the inlet tube itself. For example, the sample fluid inlet tube may be a generally L-shaped structure, with one leg of the tube extending through the wall of the tube in the region adjacent the large ends of the converging and diverging wall portions, and with another leg extending downstream along the central axis of the converging portion. This arrangement avoids the need for a very long inlet tube. As further discussed below, a short sample inlet tube minimizes the volume within the sample inlet tube and thus minimizes or avoids waste of sample suspension. This is particularly significant in certain biological tests where the sample suspension is only available in minuscule quantities.

The diverging section of the chamber serves as a means to establish a low-velocity laminar flow in the region where the tube support is located. According to further aspects of the invention, other means for establishing low-velocity laminar flow in this region can be utilized. For example, the chamber may be provided with a long, preferably straight, inlet section of constant, large cross sectional area. A downstream end of the straight section joins the converging section of the chamber wall, whereas the sheath fluid inlet is connected to the upstream end of the straight section. The inlet section has length sufficient to eliminate any turbulence in the sheath flow which may be present at the sheath fluid inlet. Because the sample suspension tube is supported in the low-velocity region adjacent the large end of the converging section, such a long inlet section can be employed while still accurately centering the sample suspension tube.

Although the transverse support for this inlet tube is located in a region of low velocity flow, and therefore low Reynolds number, the support nevertheless generates a wake. In general, when a flow that includes a wake is accelerated, the growth rate of the disturbance is considerably slower than the increase in magnitude of the mean velocity of the flow. Consequently, the relative impact of the wake decreases substantially after the flow is accelerated. The converging section of the analysis chamber accelerates the flow immediately after the region where the wake is generated by the support. Thus, the influence of the wake generated by the support in the considerably higher speed flow downstream of the support is minimal.

In another aspect of the invention, a method of forming a laminar sheath flow containing a thin sample stream is disclosed. The method comprises introducing into a flow chamber a sheath fluid flowing in a downstream direction so that the sheath fluid flows at a relatively low velocity in a first zone of the chamber. The sheath fluid is then accelerated using a converging section of the flow chamber so that the fluid flows in the downstream direction at a relatively high velocity in a second zone of the chamber downstream from the first zone. A sample fluid is introduced into the sheath fluid in the second zone from a terminus of an inlet extending into the second zone. The inlet tube is supported by means of a support extending into the chamber only in the first zone so that the fluid passes around the support at the relatively low velocity. Methods according to this aspect of the invention can provide advantages similar to those discussed above in connection with the apparatus.

BRIEF DESCRIPTION OF THE DRAWINGS

FIG. 2 is a sectional view of a pre-analysis chamber according to one embodiment of the invention;

FIG. 3 is a perspective view of a fixture according to one embodiment of the invention;

FIG. 4 is a sectional view of a pre-analysis chamber according to another embodiment of the invention;

FIG. 5 is a partial sectional view of the pre-analysis chamber of FIG. 4; and

DETAILED DESCRIPTION OF THE INVENTION

Figure 1:
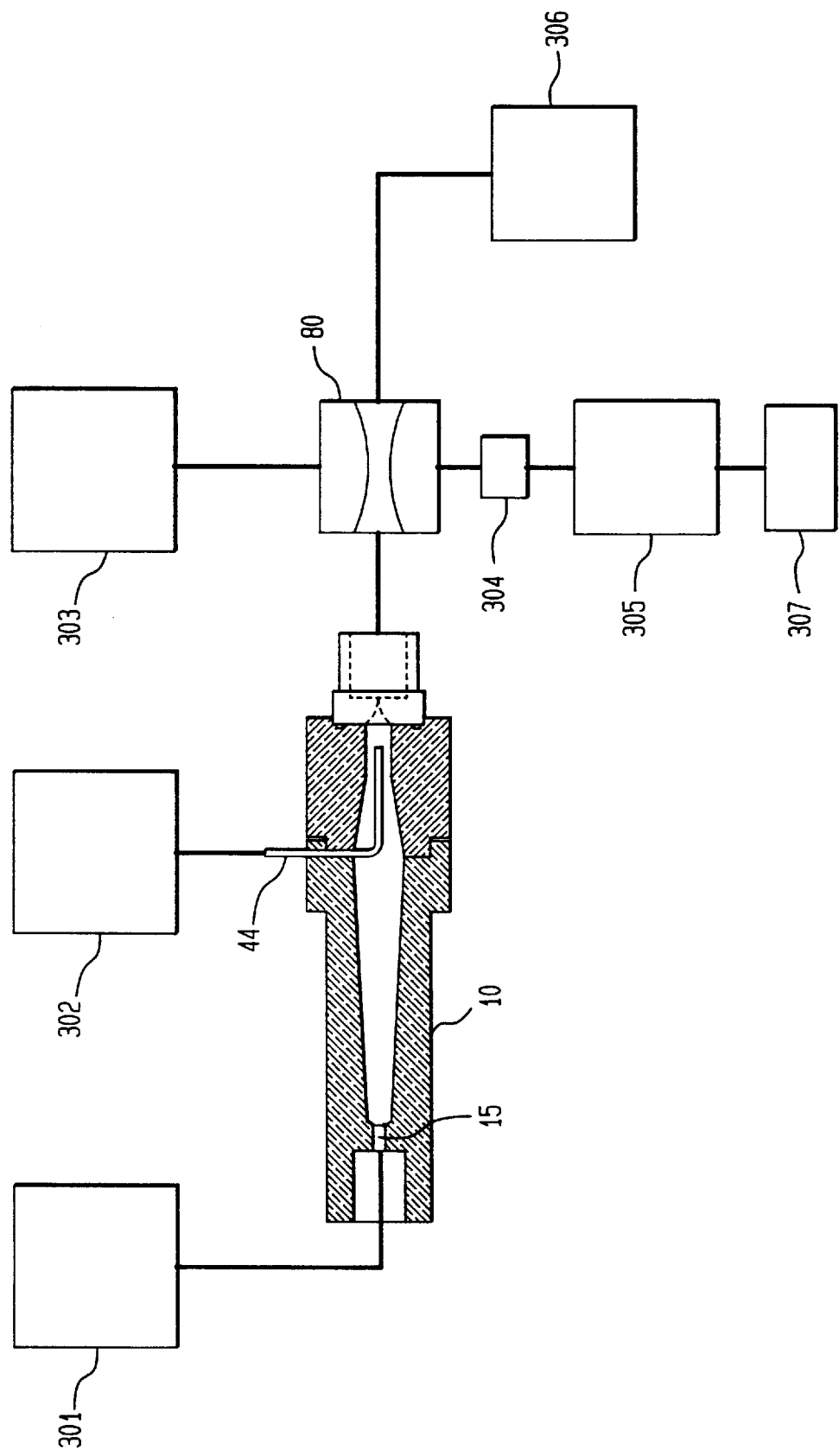
FIG. 1 is a schematic block diagram of a flow particle analyzer according to the invention.

A flow particle analyzer having a pre-analysis chamber according to the invention is shown schematically in FIG. 1. The pre-analysis chamber 10 has a sheath fluid inlet 15 for receiving sheath fluid from a sheath fluid source 301. The sheath fluid source may include a device for providing sheath fluid at a preselected flow rate, such as a syringe pump, diaphragm pump or other precision volume pump (not shown). A sample in a liquid suspension flows from a sample source 302 into a sample inlet tube 44. The sample and sheath fluid flow from the pre-analysis chamber 10, through an optical analysis chamber 80, and drain into a waste collector 306. A light source such as laser 303 provides a beam that impinges on the sample stream in the optical analysis chamber. Photosensor 304, which may be a diode array, measures scatter and/or absorption of the beam. Data from the photosensor 305 is analyzed by analysis means 307, such as a computer, to extract information about the sample from the data. The elements of the apparatus other than the pre-analysis chamber may be generally conventional.

In a preferred embodiment of the invention shown in FIG. 2, the pre-analysis chamber 10 is of three-piece construction, comprising an upstream chamber block 11, a downstream chamber block 12 and a sample inlet tube 44. The chamber blocks 11, 12 are generally cylindrical in shape and may be fabricated from 12.7 mm (½ inch) diameter heat-stabilized clear acrylic stock. In one embodiment, the diverging chamber block is approximately 31.7 mm (1¼ inch) long and the converging chamber block is approximately 12.7 mm (½ inch) long. The upstream chamber block 11 defines a central diverging chamber portion 17; the downstream chamber block defines a central converging chamber portion 31 and a cylindrical portion 32. The converging, diverging and cylindrical chamber portions are substantially axially symmetrical and substantially coaxial with one another. Thus, the chamber portions are symmetrical about a common upstream-to-downstream central axis 85.

The upstream chamber block 11 has a female pilot shoulder 33 at its downstream end for mating with a male pilot shoulder 34 on the upstream end of the downstream chamber block 12. The pilot shoulders 33, 34 mate at assembly and are fabricated to be concentric to the chamber portions 17, 31 to assure that the chamber portions mate. The blocks are joined using a cement such as a cement curable by ultraviolet radiation.

The downstream chamber block 12 has a slot 35 machined in the pilot end for receiving the sample tube 44. The sample tube is fixed in the chamber block 12 using a UV curing cement. A fixture, such as the fixture 90 shown in FIG. 3, may be used to maintain the position of the tube in the chamber while the cement is cured. The fixture 90 comprises a cylindrical body having an outer surface 93 and a bore 91. The outer surface 93 is sized to fit closely within the cylindrical portion 32. The bore 91 fits closely over the sample inlet tube 44. The bore 91 and the outer surface 93 of the fixture are machined to be concentric. To assemble the inlet tube to the downstream chamber block 12, the fixture 90 is first inserted into the cylindrical portion 32 of the chamber from the downstream end. A longitudinal portion 42 of the sample inlet tube 44 is then inserted into the bore 91 of the fixture 90, establishing a position of the inlet tube along the central axis 85 of the chamber. A transverse portion 40 of the inlet tube may then be cemented into the slot 35 while maintaining the position of the tube in the chamber. The fixture 90 is removed after the cement has cured.

A sheath fluid inlet 15 communicates with the diverging chamber portion 17 at its upstream end. A step 19 is provided for ease of manufacture; however, such a step should be minimized to minimize flow separation after the inlet 15. Inlet 15 is connected to a source 301 (FIG. 1) of the sheath fluid. Counter-bore 16 in the chamber block 11 provides clearance for a supply line connector (not shown).

In a preferred embodiment of the invention, the chamber wall 18 of the diverging chamber 17 is conical and has a maximum angle of about 7 degrees. This angle has been found to maximize deceleration without inducing flow separation.

The diverging chamber portion 17 of the upstream block 11 communicates with a converging chamber portion 31 in the downstream block 12 at a junction surface 20. In a preferred embodiment, the diameter of the chambers at junction surface 20 is approximately 4.8 mm (3/16 inch). The converging chamber 31 is defined by a preferably conical chamber wall 30 having an included angle of approximately 20 degrees, which accelerates sheath fluid before it enters the cylindrical portion 32.

In the preferred embodiment shown in FIG. 2, sample inlet tube 44 is preferably fabricated from stainless steel tubing having an inside diameter of approximately 0.5 mm (0.020 inches). A transverse portion 40 of the inlet tube 44 enters the sheath flow stream near the junction surface 20 after passing through the slot 35 in the chamber block 12, as described above. The sample inlet tube has no support downstream from transverse portion 40. Stated another way, the only support for the first portion of the sample inlet tube is disposed adjacent the large end of the converging section; no supports are positioned downstream from the large end of the converging section, either adjacent the small end of the converging section, or in the cylindrical portion 32. Adjacent the central axis 85 of the chamber portion 31, the inlet tube bends 90 degrees at bend 41. A longitudinal portion 42 of the tube extends from the bend 41 through the converging portion 31 of the chamber and ends within a cylindrical portion 32 of the chamber at a terminus 43. The terminus 43 has a rounded outside diameter to minimize the attachment of small bubbles that could slightly shift the sample stream. The terminus 43 may also be tapered (not shown) to reduce the wake produced by the tube. Portion 42 is substantially coaxial with the central axis 85 defined by the chamber wall. In another embodiment of the invention (not shown), the terminus 43 of the sample inlet tube 44 is located within the converging chamber 31. In this arrangement, the continued acceleration of the fluid after passing the terminus 43 of the inlet tube reduces the impact of the wake formed by the terminus as the flow velocity increases.

In a method of operation according to one embodiment of the invention, the sheath fluid supplied by source 301 enters the diverging chamber 17 from inlet 15 without changing flow direction, minimizing turbulence introduced in the fluid as it enters the chamber. As the sheath fluid passes through the diverging chamber portion 17, the fluid is decelerated. At the same time, the relatively low divergence angle of the chamber 17 does not induce flow separation at the chamber wall 18, and a laminar flow profile is maintained. At the junction surface 20, the sheath flow has a laminar, relatively low-velocity profile. Because the transverse portion of the sample tube extends into the chambers at the point of least cross-flow velocity, the wake disturbance caused by the tube is minimized.

As the sheath fluid passes downstream, away from the vicinity of juncture plane 20 and transverse portion 40, the sheath fluid is progressively accelerated in converging portion 31, and thus enters portion 32 at a relatively high velocity. Any minor flow disturbances produced at transverse section 40 are substantially attenuated as the flow velocity is increased through the converging portion of the chamber, before the sheath fluid reaches cylindrical portion 32.

A liquid sample containing particles to be analyzed, such as agglutinated and non-agglutinated particles from a biochemical test, is introduced by sample source 302 through the sample inlet tube 44 into the cylindrical portion 32. Because the sample is introduced in a region of laminar flow, it does not mix with the sheath fluid to any appreciable extent, but instead forms a discrete stream surrounded by the flowing sheath fluid. The sample is introduced at a velocity lower than that of the sheath fluid in the cylindrical portion 32 of the chamber. Because the cross-sectional area of a flow stream decreases with increasing velocity at a constant flow rate, the sample stream is further thinned as it accelerates to the sheath fluid velocity. The sheath fluid and the sample stream are further reduced in cross-section by nozzle 81 before entering the analysis chamber. For flow particle analysis, the sample stream preferably has a transverse dimension in the analysis chamber that approaches the particle size in order to assure that the particles are presented one at a time. In one example, particles having a diameter of from 1 to 2.2 microns are entrained in a sample stream having a diameter of from 1 to 2 microns.

As can be seen in FIG. 2, the sheath fluid flows through the chamber 10 in a generally uniform direction from the inlet 11, though the chamber portions 17, 32, to the optical analysis chamber 80 at the downstream end of the chamber. The sheath fluid does not encounter bends or changes in direction that may induce turbulence in the flow stream.

In another embodiment of the invention, shown in cross section in FIG. 4, the pre-analysis chamber 100 comprises an inlet tube support 101 extending from the chamber wall 104 and securing a long sample inlet tube 102. The inlet tube 102 enters the rear 103 of the chamber 105 and extends centrally along its length. Alternatively, the inlet tube 102 may enter the chamber 105 at a point intermediate the rear 103 and the junction surface 107. The support 101 maintains the terminus 106 of the tube at a central location within the chamber. The support 101 traverses the sheath flow profile at the junction surface 107 where the laminar, low velocity sheath flow is not significantly disrupted by the support. As in the embodiment of FIGS. 1–2, a stable, laminar flow of sheath fluid passes the terminus 106 of the inlet tube 102. As seen in FIG. 5, the inlet tube support 101 may have a streamlined cross section to further minimize disruptions to the flow profile. For example, the support 101 shown in FIG. 5 has a rounded leading edge 111 and a pair of sloping walls 110 tapering toward one another in the downstream direction.

Figure 6:
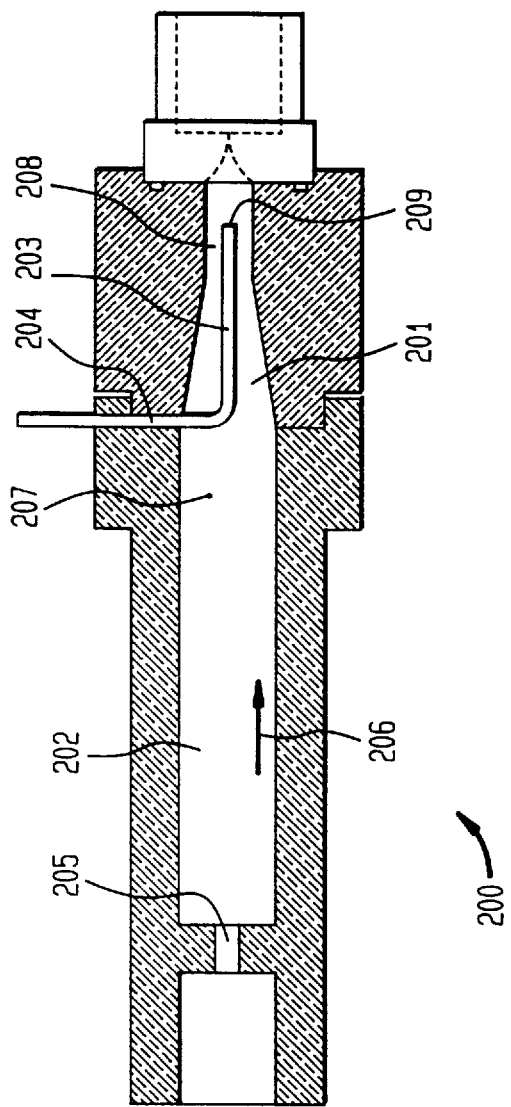
FIG. 6 is a sectional view of another embodiment of a pre-analysis chamber according to a further embodiment of the invention.

FIG. 6 is a cross sectional view of an embodiment of the invention comprising a pre-analysis chamber 200 having a long chamber of constant cross section 202 for establishing a low velocity, laminar flow in the upstream portion of the converging chamber. Sheath fluid introduced through a sheath fluid inlet 205 flows into chamber 202 and gradually forms a stable, low-velocity laminar profile as it moves through the chamber. Because of these favorable sheath flow conditions, the profile is only minimally affected by the transverse portion 204 of the inlet tube 203.

Thus, the sheath flow is first introduced through the inlet 205 into a flow chamber 202 flowing downstream in a first direction 206 so that the sheath fluid flows in the first direction at a relatively low velocity in a first zone 207 of the chamber. The sheath fluid is then accelerated by means of a converging section 201 of the flow chamber so that it flows at a relatively high velocity in a second zone 208 of the chamber. The sample is introduced into the sheath fluid in the second zone 208 from a terminus 209 of an inlet tube 203. The transverse potion of the inlet tube extends into the chamber only in the first zone 207 so that the fluid passes around it at a relatively low velocity.

The flow chamber 202 of the method may be a long chamber of constant cross section, or may be a diverging chamber as described above. Because the sample inlet tube need not be supported from the rear or upstream end of the chamber, it is possible to provide a very long constant cross section chamber, sufficient to produce proper laminar flow, while still maintaining accurate positioning of the sample tube tip. Moreover, because the sample tube enters the chamber close to the downstream end, there is no need to provide a long sample tube. Therefore, the device can have very low sample holdup even where a long chamber is employed to provide laminar sheath flow. Other means for producing a low velocity, laminar flow profile at the support can be used.

Although particular embodiments of the present invention have been shown and described, many varied embodiments incorporating the teachings of the present invention easily may be constructed by those skilled in the art.

We claim:

1. A pre-analysis chamber for a flow particle analyzer, comprising:

a chamber wall with diverging and converging portions having respective large ends interconnected, said diverging and converging portions having small ends remote from one another;

a sheath fluid inlet connected adjacent a small end of said diverging portion;

a first portion of a sample inlet tube extending within said converging portion of said chamber wall and having a discharge end disposed adjacent a small end of said converging chamber wall portion;

a tube support extending from said chamber wall to said first portion of said sample inlet tube adjacent said large ends; and an outlet adjacent said small end of said converging portion.

2. The pre-analysis chamber of claim 1 wherein said converging portion of said chamber wall is substantially symmetrical about an upstream-to-downstream axis, and wherein said first portion of said sample inlet tube extends substantially parallel to said axis.

3. The pre-analysis chamber of claim 2 wherein said first portion of said sample inlet tube is substantially coaxial with said converging portion of said chamber wall.

4. The pre-analysis chamber of claim 2 wherein said diverging portion of said chamber wall is also substantially symmetrical about said upstream-to-downstream axis.

5. The pre-analysis chamber of claim 1, wherein said tube support comprises a second portion of said sample inlet tube.

6. The pre-analysis chamber of claim 1, further comprising a portion of said chamber wall having a uniform cross section in alignment with said converging portion, wherein said sample inlet tube terminates within said uniform portion, said uniform portion defining said outlet.

7. The pre-analysis chamber of claim 1, wherein said diverging portion of said chamber wall has a first conical shape.

8. The pre-analysis chamber of claim 7, wherein said first conical shape has an included angle of about 7 degrees.

9. The pre-analysis chamber of claim 1, wherein said converging portion of said chamber wall has a second conical shape.

10. The pre-analysis chamber of claim 9, wherein said second conical shape has an included angle of about 20 degrees.

11. The pre-analysis chamber of claim 1, wherein said diverging portion of said chamber wall comprises a passageway in a first chamber block, and said converging portion of said chamber wall comprises a passageway in a second chamber block.

12. The pre-analysis chamber of claim 11, wherein said chamber blocks are acrylic.

13. The pre-analysis chamber of claim 11, wherein said first and second chamber blocks further comprise first and second pilot elements for aligning said converging and diverging portions of said chamber wall.

14. The pre-analysis chamber of claim 11, wherein one of said first and second chamber blocks has a groove adjacent said passageway for receiving said tube support.

15. A chamber for a flow particle analyzer, comprising:

a chamber wall having a diverging portion and a converging portion coaxial with and downstream of said diverging portion;

a sample inlet tube having a first portion coaxial with said chamber wall; and a support attaching said inlet tube to said wall proximate a region between said diverging and converging portions.

16. The chamber of claim 15, wherein said support is a second portion of said inlet tube substantially perpendicular to said first portion.

17. The chamber of claim 15, further comprising a sheath fluid inlet coaxial with and upstream of said chamber wall.

18. The chamber of claim 15, wherein said first portion of said sample tube terminates downstream of said converging portion of said chamber wall.

19. The chamber of claim 15, wherein said first portion of said sample tube terminates within said converging portion of said chamber wall.

20. A pre-analysis chamber for a flow particle analyzer, comprising:

means for establishing substantially laminar, low velocity flow in a downstream direction;

a chamber wall defining a converging section with large and small ends, said converging section connected at its large end to said flow establishing means so that the laminar flow in the downstream direction will enter the large end of the converging section and will pass downstream to the small end;

a sample inlet tube including a discharge portion of said sample inlet tube disposed within said chamber wall; and a tube support proximate said large end of said converging section, said tube support being positioned in the downstream laminar flow established by the means for establishing substantially laminar, low velocity flow.

21. The chamber of claim 20, wherein said means for establishing substantially laminar, low velocity flow comprises a gradually diverging chamber wall.

22. The chamber of claim 20, wherein said means for establishing substantially laminar, low velocity flow comprises a long chamber of substantially constant cross section.

23. The chamber of claim 20 wherein said sample tube includes a support portion extending transverse to said converging chamber wall.

24. The chamber of claim 20 wherein said converging section defines a downstream direction towards said small end and an upstream direction toward said large end, said sample inlet tube being unsupported downstream from a region proximate said large end of said converging section.

25. A method of forming a laminar sheath flow containing a thin sample stream, comprising:

introducing into a flow chamber a sheath fluid flowing downstream in a first direction so that the sheath fluid flows in said first direction in laminar flow at a first velocity in a first zone of said chamber;

accelerating the sheath fluid by means of a converging section of said flow chamber so that the fluid flows in said first direction at a second velocity higher than said first velocity in a second zone of said chamber downstream from said first zone; and introducing a sample fluid into said sheath fluid in said second zone from a terminus of an inlet tube extending into said second zone while supporting said inlet tube by means of a support extending into the chamber only in said first zone so that the sheath fluid passes around the support at said first velocity.

26. The method of claim 25, wherein the step of introducing said sheath fluid so that it flows at a first velocity comprises introducing said sheath fluid at a small end of a diverging taper and gradually decelerating said fluid through said taper to said first zone.

27. The method of claim 26, wherein said diverging taper has an included angle of approximately 7 degrees.

28. The method of claim 25, wherein said converging section has an included angle of approximately 20 degrees.

29. The method of claim 25, wherein said sample is introduced at a velocity lower than said second velocity of said sheath fluid in said second zone.

30. The method of claim 25, wherein the step of introducing said sheath fluid at a first velocity comprises introducing said sheath fluid at an upstream end of a long chamber of constant cross section and permitting the sheath fluid to form a laminar flow profile before reaching said first zone.

* * * * *